United States Patent
Liu

(10) Patent No.: US 9,458,823 B2
(45) Date of Patent: Oct. 4, 2016

(54) WIND TURBINE BLADE SHEAR WEB CONNECTION ASSEMBLY

(75) Inventor: Lihua Liu, XuanZhou (CN)

(73) Assignee: General Electric Company, Schenectady, NY (US)

(*) Notice: Subject to any disclaimer, the term of this patent is extended or adjusted under 35 U.S.C. 154(b) by 313 days.

(21) Appl. No.: 14/353,784

(22) PCT Filed: Dec. 12, 2011

(86) PCT No.: PCT/CN2011/083808
§ 371 (c)(1),
(2), (4) Date: Apr. 24, 2014

(87) PCT Pub. No.: WO2013/086667
PCT Pub. Date: Jun. 20, 2013

(65) Prior Publication Data
US 2014/0294591 A1    Oct. 2, 2014

(51) Int. Cl.
*F01D 5/14* (2006.01)
*F03D 1/06* (2006.01)
*F16B 2/10* (2006.01)
*F16B 11/00* (2006.01)
*A61F 13/15* (2006.01)
*B64C 27/473* (2006.01)

(52) U.S. Cl.
CPC .......... *F03D 1/0675* (2013.01); *F03D 1/0683* (2013.01); *F16B 2/10* (2013.01); *F16B 11/008* (2013.01); *A61F 13/15593* (2013.01); *B64C 27/473* (2013.01); *Y02E 10/721* (2013.01); *Y10T 403/473* (2015.01)

(58) Field of Classification Search
CPC .................. Y10T 403/4602; Y10T 403/4605; Y10T 403/4621; Y10T 403/473

USPC ................ 156/160, 293; 248/316.5; 416/226
See application file for complete search history.

(56) References Cited

U.S. PATENT DOCUMENTS 5,476,704 A * 12/1995 Kohler ................. B29C 66/721
                                                          244/119
6,513,757 B1    2/2003 Amaoka et al.
6,520,706 B1 *  2/2003 McKague, Jr. ....... B29C 70/342
                                                           156/148

(Continued)

FOREIGN PATENT DOCUMENTS

WO    WO 2009/155920 A1    12/2009

OTHER PUBLICATIONS

DK Office Action issued in connection with related Application No. PA201470278 on Sep. 23, 2014.

*Primary Examiner* — Robert K. Arundale
(74) *Attorney, Agent, or Firm* — Dority & Manning, P.A.

(57) ABSTRACT

A wind turbine blade has upper and lower shell members with a respective spar cap configured on an internal face of the shell members. A shear web extends between the spar caps along a longitudinal length of the blade. A connection assembly is configured between the transverse ends of the shear web and the spar caps and includes a channel structure configured on the spar cap. The channel structure includes side walls that extend from the spar cap along the longitudinal sides of the shear web. A pliant actuation line is attached between the side walls of the channel structure and bond paste is deposited in the channel structure. Movement of the transverse end of the shear web into the channel structure results in the actuation line pulling the side walls of the channel structure against the longitudinal sides of the shear web.

13 Claims, 4 Drawing Sheets

(56) References Cited

U.S. PATENT DOCUMENTS

| | | | |
|---|---|---|---|
| 6,945,727 B2 | 9/2005 | Christman et al. | |
| 7,037,568 B1 | 5/2006 | Rogers et al. | |
| 7,244,487 B2 | 7/2007 | Brantley et al. | |
| 7,371,304 B2 * | 5/2008 | Christman | B29C 65/00 156/293 |
| 7,393,488 B2 * | 7/2008 | Grose | B29C 65/527 264/254 |
| 7,841,835 B2 | 11/2010 | Bagepalli et al. | |
| 7,897,095 B2 * | 3/2011 | Raeckers | B29C 65/5042 156/242 |
| 8,235,671 B2 | 8/2012 | Yarbrough | |
| 8,257,048 B2 | 9/2012 | Yarbrough | |
| 8,262,362 B2 | 9/2012 | Yarbrough | |
| 8,393,871 B2 | 3/2013 | Yarbrough | |
| 2003/0037867 A1 | 2/2003 | Bersuch et al. | |
| 2006/0225278 A1 * | 10/2006 | Lin | F03D 1/001 29/889.72 |
| 2007/0110584 A1 | 5/2007 | Stommel | |
| 2010/0135815 A1 * | 6/2010 | Bagepalli | F03D 1/0675 416/226 |
| 2010/0162567 A1 | 7/2010 | Kirkwood et al. | |
| 2011/0008175 A1 | 1/2011 | Gau | |
| 2011/0142663 A1 | 6/2011 | Gill | |
| 2011/0142674 A1 | 6/2011 | Dixon et al. | |
| 2011/0211969 A1 | 9/2011 | Nies | |
| 2011/0211970 A1 | 9/2011 | Nies | |
| 2012/0027610 A1 | 2/2012 | Yarbrough | |
| 2012/0027612 A1 * | 2/2012 | Yarbrough | F03D 1/065 416/226 |
| 2012/0027613 A1 * | 2/2012 | Yarbrough | F03D 1/065 416/226 |
| 2012/0027614 A1 * | 2/2012 | Yarbrough | F03D 1/065 416/226 |
| 2012/0027615 A1 * | 2/2012 | Irizarry-Rosado | F03D 1/0675 416/226 |
| 2014/0064980 A1 * | 3/2014 | Griesel | F03D 1/0675 416/226 |
| 2015/0152838 A1 * | 6/2015 | Merzhaeuser | F03D 1/0675 416/226 |
| 2015/0316026 A1 * | 11/2015 | Noronha | F03D 1/0675 416/226 |

* cited by examiner

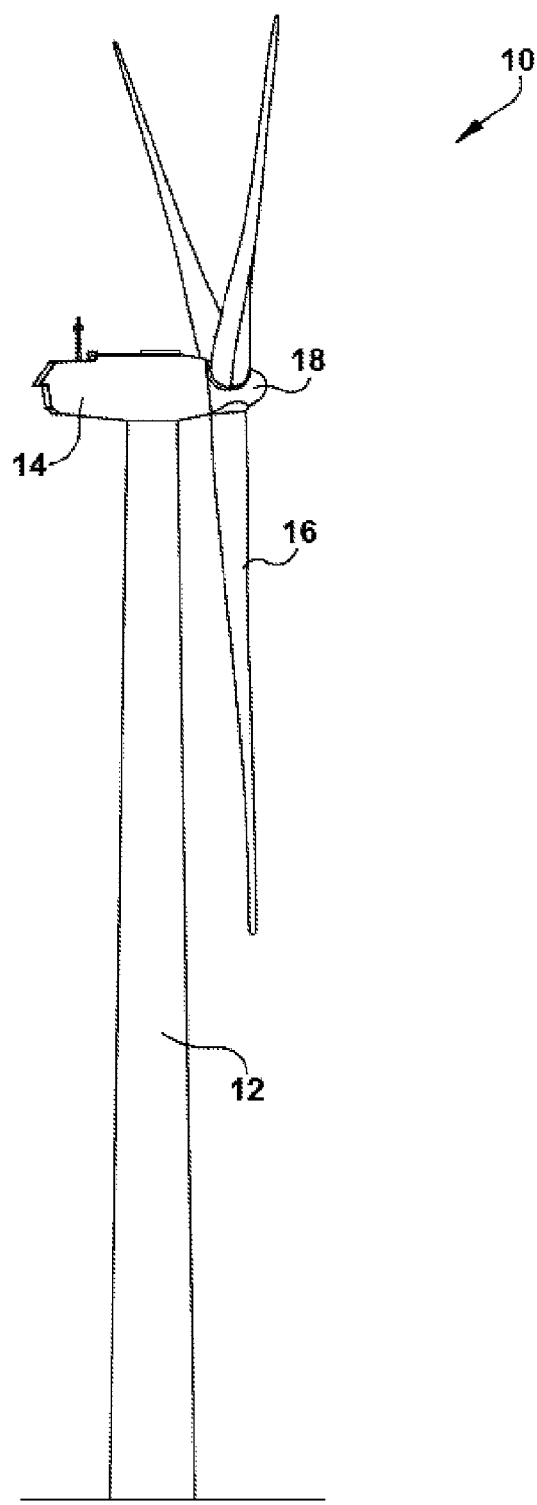
Fig. -1-
Prior Art

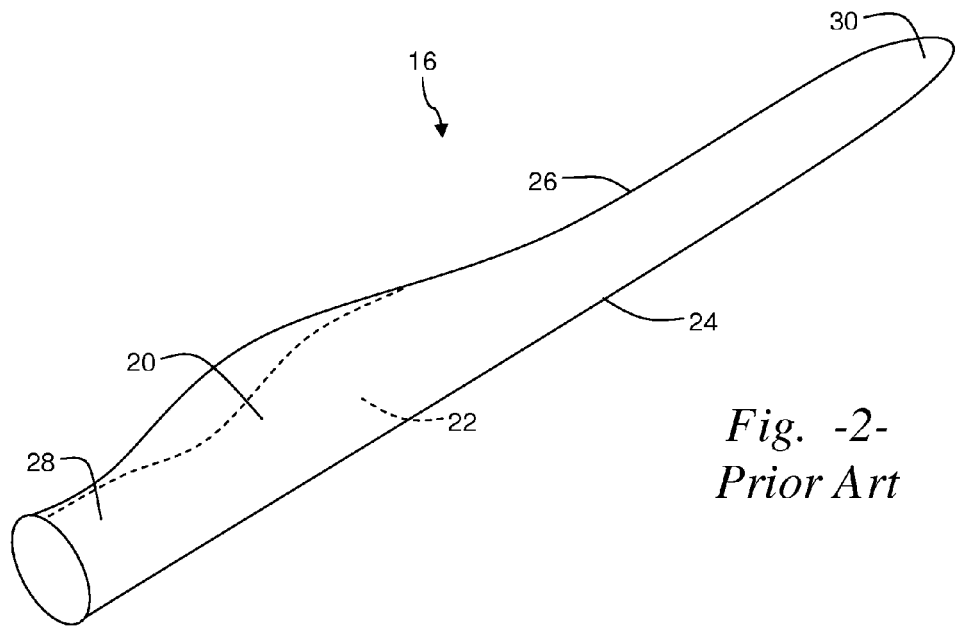
Fig. -2-
Prior Art
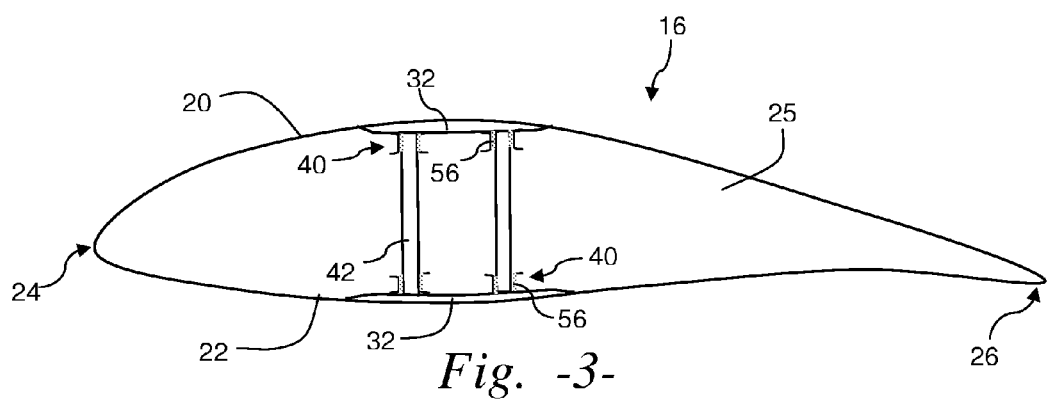
Fig. -3-

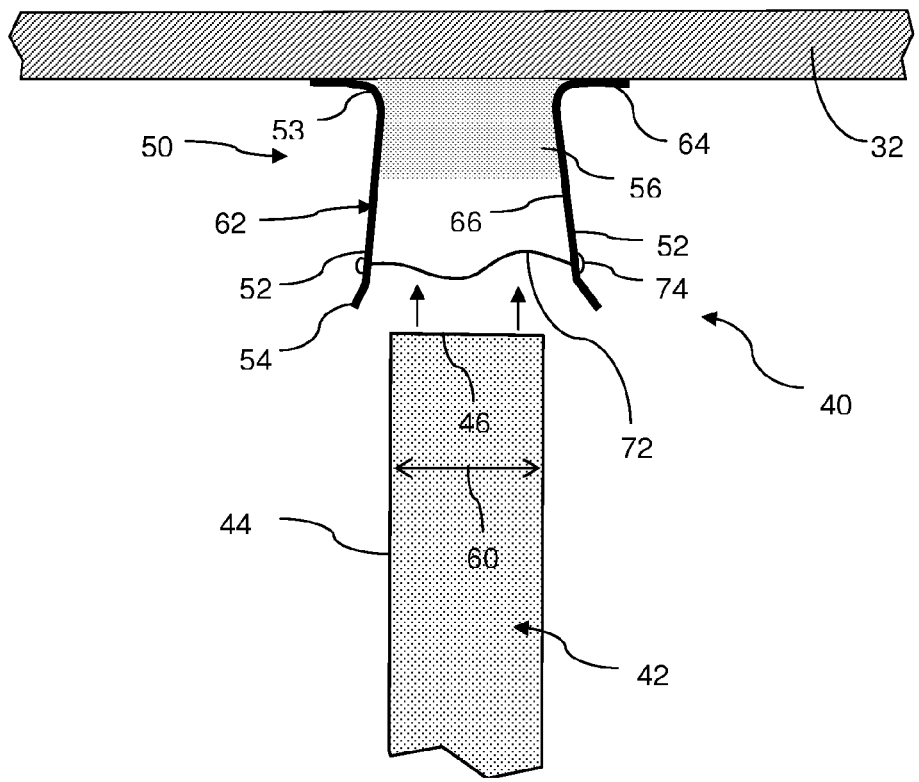
Fig. -4-
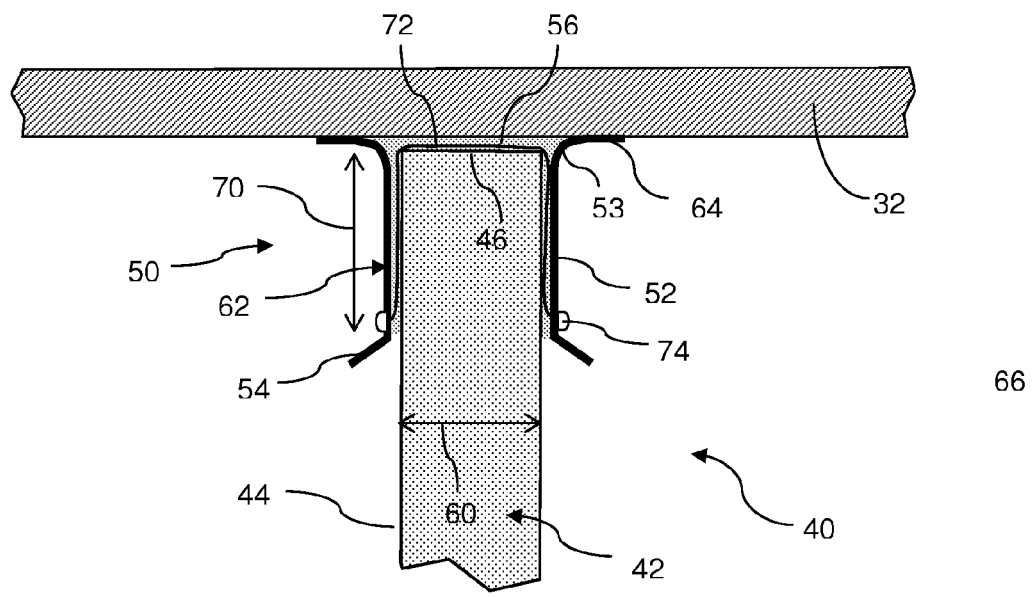
Fig. -5-

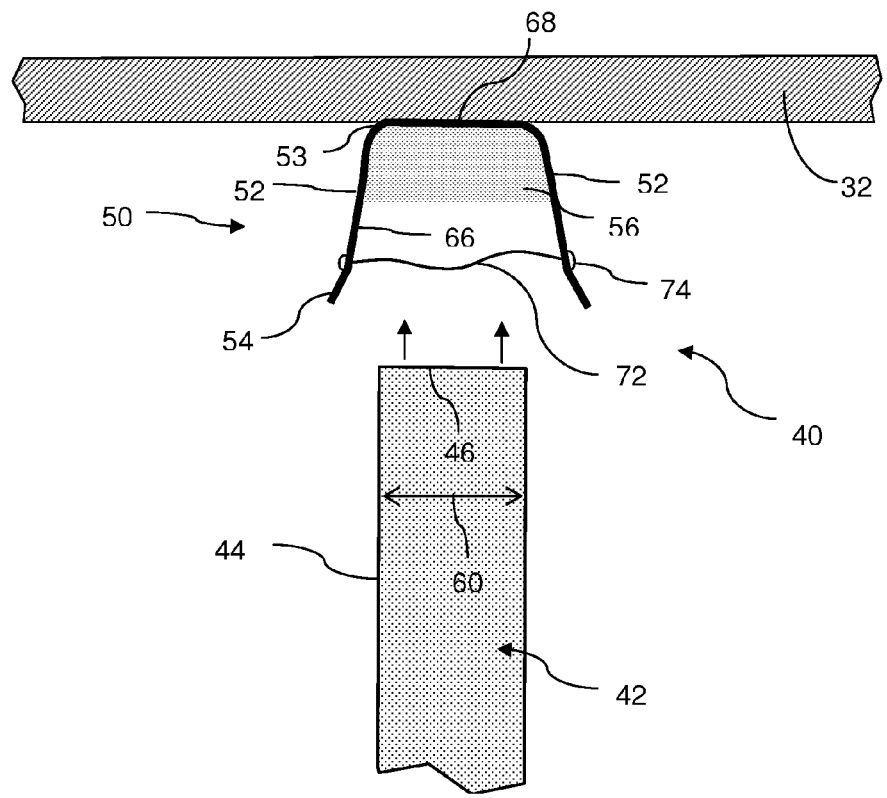
Fig. -6-
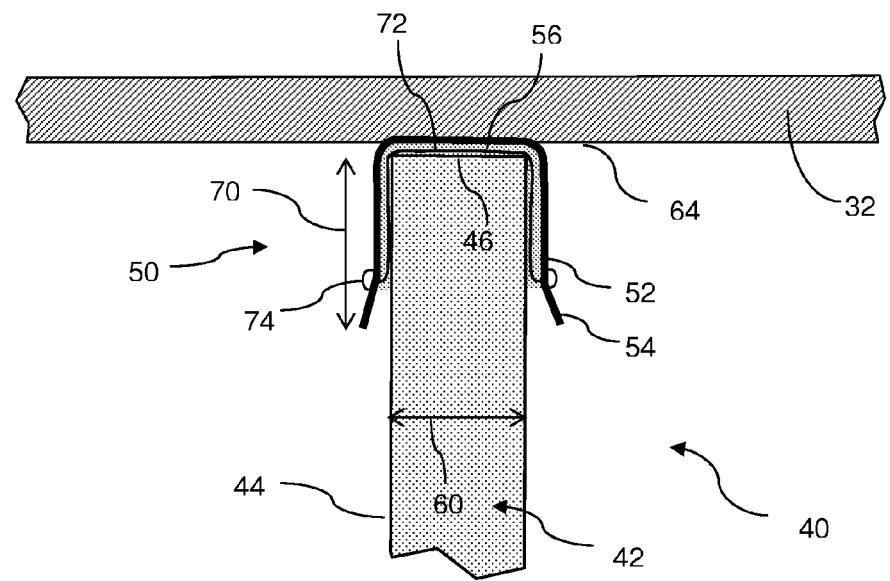
Fig. -7-

WIND TURBINE BLADE SHEAR WEB CONNECTION ASSEMBLY

FIELD OF THE INVENTION

The present invention relates generally to the field of wind turbines, and more particularly to the shear web configuration within the wind turbine blades.

BACKGROUND OF THE INVENTION

Turbine blades are the primary elements of wind turbines for converting wind energy into electrical energy. The blades have the cross-sectional profile of an airfoil such that, during operation, air flows over the blade producing a pressure difference between the sides. Consequently, a lift force, which is directed from a pressure side towards a suction side, acts on the blade. The lift force generates torque on the main rotor shaft, which is geared to a generator for producing electricity.

The turbine blades typically consist of a suction side shell and a pressure side shell that are bonded together at bond lines along the trailing and leading edges of the blade. An internal shear web extends between the pressure and suction side shell members and is bonded to spar caps affixed to the inner faces of the shell members. Relatively exact length dimensions are required for the spar web to span between the spar caps and to achieve a bond with the spar cap having sufficient width and thickness dimensions. Achieving these dimensions, as well as an adequate bond, can be difficult and the juncture between the spar caps and shear web is a time-consuming and tedious process that often requires significant re-work.

With typical blade constructions, a rigid flange is used to achieve the desired bond width for bond paste applied between the spar caps and transverse ends of the shear web. This configuration, however, requires relatively precise placement of the shear web relative to the flanges and does not accommodate relatively large length variances (e.g., shortages) in the shear web and often results in the use of excess bond paste to make up for a length deviation and to achieve the bond width. The excess paste contributes unnecessary weight to the blade and can break off and result in blade "rattling" during operation of the wind turbine (a not uncommon complaint from wind turbine owners/operators). Also, air voids and unpredictable squeeze-out of the bond paste in the typical construction can result in areas of decreased bond strength, which is particularly problematic in sections of the blade where repair is not possible from within the blade.

Accordingly, the industry would benefit from an improved bond configuration between the shear web and spar caps that addresses one or more of the deficiencies of certain conventional configurations.

BRIEF DESCRIPTION OF THE INVENTION

Aspects and advantages of the invention will be set forth in part in the following description, or may be obvious from the description, or may be learned through practice of the invention.

In accordance with aspects of the invention, a wind turbine blade includes an upper shell member having a spar cap configured on an internal face thereof, and a lower shell member having a spar cap configured on an internal face thereof. A shear web extends between the spar caps along a longitudinal length of the blade. A connection assembly is provided between transverse ends of the shear web and the spar caps and includes a channel structure affixed to the spar cap by any suitable means. The channel structure has side walls that extend from the spar cap along longitudinal sides of the shear web. The side walls are initially flexed outwardly at an angle from spar cap away from the longitudinal sides of shear web and are flexible so as to move into engagement against the longitudinal sides of the shear web. A pliant actuation line, such as a string, chord, cable, and the like, is attached between the side walls of the channel structure. Bond paste is deposited in the channel structure and, upon movement of the transverse end of the shear web into the channel structure, the shear web engages the actuation line and pulls the side walls into engagement against the longitudinal sides of the shear web with the bond paste being distributed between the side walls and sides of the shear web.

With movement of the transverse end of the shear web into the channel structure, Bond paste is displaced between the channel structure side walls and the longitudinal sides of the shear web. Thus, an effective bond length is created between the shear web and channel structure side walls that is proportional to the length of the bond between each of the side walls and the side of the shear web. In a particular embodiment, the length of the bond along each of the side walls may be greater than the width of the transverse end of the shear web, thereby producing a substantially greater total bond strength.

The channel structure may be variously configured. In one embodiment, the side walls have a base portion and are spaced apart at the bases a width that is generally equal or slightly greater than the width of the shear web. The side walls are flexed outwardly from the base for insertion of the shear web into the channel structure. The side walls may include a flared end to accommodate flexing and receipt of the shear web.

In still a further embodiment, the channel structure may be a multi-component assembly. For example, each of the channel structure side walls may be separate components that are individually attached to the spar cap. In this type of embodiment, the channel structure side walls may be configured as flange members bonded to the spar cap so as to extend transversely therefrom, with the spar cap exposed between the side walls. With this embodiment, the transverse end of the shear web may be encased in bond paste and bonded directly to the spar cap within the channel structure.

In an alternate embodiment, the channel structure may be a single, unitary component, for example a U-shaped component, and include an end wall extending between the side walls, with the end wall affixed to the spar cap. With this embodiment, the transverse end of the shear web may be encased in bond paste completely within the channel structure.

The present invention also encompasses various method embodiments for connecting a shear web between spar caps of upper and lower shell members in a wind turbine blade. The method includes locating a channel structure on each of the spar caps at an attachment location for the shear web, with the channel structures having sides walls that flex outwardly relative to longitudinal sides of the shear web. An actuation line is attached between the sides walls of the channel structure. Bond paste is deposited into the channel structure between the side walls. A transverse end of the shear web is inserted into the channel structure and engages the actuation line such that further movement of the transverse end into the channel structure causes the sides walls to flex inwardly and engage against the longitudinal sides of the shear web with the bond paste being displaced and distributed between the side walls and longitudinal sides of the shear web.

In a particular embodiment, the method includes defining the channel structure by attaching separate spaced-apart members to the spar cap, with the spar cap exposed between the members and the transverse end of the shear web bonded to the spar cap between the members. In an alternate embodiment, the channel structure is defined by attaching a single integral component to the spar cap, with the component having an end wall attached to the spar cap. The transverse end of the shear web is spaced from the end wall and is encased in bond paste within the channel structure.

The method may include providing the actuation line with any combination of length and elasticity so that the transverse end seats completely within the channel structure with the side walls engaged against the longitudinal sides of the shear web.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art is set forth in the specification, which makes reference to the appended figures, in which:

FIG. 1 is a perspective view of a conventional wind turbine;

FIG. 2 is a perspective view of a conventional wind turbine blade;

FIG. 3 is a cross-sectional view of an exemplary wind turbine blade incorporating aspects of the invention;

FIG. 4 is an enlarged cross-sectional component view of a connection assembly between a shear web and spar cap in accordance with an embodiment of the invention;

FIG. 5 is an enlarged cross-sectional view of the embodiment of FIG. 4; in an assembled state;

FIG. 6 is an enlarged cross-sectional component view of an alternate embodiment of a connection assembly; and, FIG. 7 is an enlarged cross-sectional component view of still another embodiment of a connection assembly.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention include such modifications and variations as come within the scope of the appended claims and their equivalents.

FIG. 1 illustrates a wind turbine 10 of conventional construction. The wind turbine 10 includes a tower 12 with a nacelle 14 mounted thereon. A plurality of turbine blades 16 are mounted to a rotor hub 18, which is in turn connected to a main flange that turns a main rotor shaft. The wind turbine power generation and control components are housed within the nacelle 14. The view of FIG. 1 is provided for illustrative purposes only to place the present invention in an exemplary field of use. It should be appreciated that the invention is not limited to any particular type of wind turbine configuration.

FIG. 2 is a more detailed view of a wind turbine blade 16. The blade 16 includes an upper shell member 20 and a lower shell member 22. The upper shell member 20 may be configured as the suction side surface of the blade 16, while the lower shell member 22 may be configured as the pressure side surface of the blade. The blade 16 includes a leading edge 24 and a trailing edge 26, as well as a root portion 28, and a tip portion 30. As is well known in the art, the upper shell member 20, and lower shell member 22 are joined together at the leading edge 24 and trailing edge 26. The blade 16 includes an internal cavity 25 (FIG. 3) in which various structural members, such as spar caps and one or more shear webs, are configured.

FIG. 3 is a cross-sectional view of a wind turbine blade 16 that incorporates aspects of the invention. The blade 16 includes one or more internal structural shear webs 42 that span between the upper 20 and lower shell members 22. In particular, the shear webs 42 span between structural spar caps 32 that are fixed to the internal faces of the shell members 20, 22. In accordance with aspects of the invention, an improved connection assembly 40 is provided at the interface of the shear webs 42 and spar caps 32, as described in greater detail below.

FIGS. 4 and 5 depict an embodiment of a connection assembly 40 between transverse ends 46 of the shear web 42 and the spar caps 32. The connection assembly 40 includes a channel structure 50 configured on the spar cap 32. The channel structure 50 has side walls 52 that extend transversely from the spar cap 32 at an angle away from the longitudinal sides 44 of the shear web 42. The side walls 52 may be relatively rigid members that are flexed outwardly relative to the longitudinal sides 44. The side walls 52 may flex at a pivot or flexure point 53 that is formed in the walls, for example by a relief. Bond paste 56 is disposed within the channel structure 50, as depicted by the shaded areas in the figures. The bond paste 56 may be applied as a continuous or discontinuous layer between the members, and in any amount to achieve an overall desired bond paste thickness and strength between the shear web 42 and spar caps 32 in the assembled state (FIG. 5).

An actuation line 70 is connected between the side walls 52 of the channel structure 50. This line 70 may be, for example, any manner of string, cord, ribbon, cable, or other pliant member. The line 70 may be connected to an inner face 66 of the side walls 52, or may extend through the walls 52 and be attached with any suitable external fastener 74. The line 70 may be generally inelastic with a fixed length, or may have a degree of elasticity so as to stretch to the position depicted in FIG. 5.

Upon insertion of the transverse end 46 of the shear web 42 into the channel structure 50 (between the side walls 54), the end 46 engages the actuation line 70. Further movement of the transverse end 46 into the channel structure 50 causes the side walls 54 to be pulled inwardly towards the longitudinal sides 44 of the shear web, as should be readily appreciated from FIGS. 4 and 5. The line 70 has any combination of length and elasticity such that when the transverse end 46 is seated within the channel structure 50, the side walls 54 are pulled into engagement against the sides 44.

Insertion of the transverse end 46 into the channel structure 50 results in displacement and distribution of the bond paste around the transverse end 46 and between the side walls 54 and longitudinal sides 44 of the shear web. An effective bond length 70 is created between the shear web 42 and a respective one of the side walls 52. The total bond between the shear web 42 and spar cap 32 is thus proportional to the combined length of the bonds 70 between each of the side walls 52 and the side of the shear web sides 44. In the embodiment of FIGS. 4 and 5, the length 70 of the bond along each of the side walls 52 is greater than the width 60 of the transverse end 46 of the shear web, thereby producing a substantially greater total bond strength as compared to a bond layer between the transverse end 46 and spar cap 32.

The channel structure 50 may be variously configured. For example, in the embodiment of FIGS. 4 and 5, the rigid side walls 52 are spaced apart with a width 58 that is less than the shear web width 60 (at least at the open receiving end of the channel structure 50). In this configuration, the side walls 52 flex outwardly for insertion of the shear web 42 into the channel structure, as in evident from the view of FIG. 5. Thus, a positive engagement of the side walls 52 against the shear web sides 44 is provided. The side walls 52 may include a flared receiving end 54 to accommodate flexing and receipt of the shear web 42.

The channel structure 50 may be a multi-component assembly, as depicted in the embodiments of FIGS. 4 through 6. For example, each of the channel structure side walls 52 may be separate components that are individually affixed to the spar cap 32 at a base portion of the side walls. For example, in the illustrated embodiment, the channel structure side walls 52 are configured as individual flange members 62 having an attachment leg 64 affixed to the spar cap 32 by suitable means, such as bonding, mechanical fasteners, and so forth. The flange members 62 include an inner or bond face 66 that extends transversely from the spar cap 32 along the shear web sides 44.

In the embodiment of FIGS. 6 and 7, the channel structure 50 is a single, unitary component, for example a U-shaped channel component, and includes an end wall 68 that extends between the side walls 52. The end wall 68 is affixed to the spar cap 32 by any suitable means. The U-shaped channel component thus forms a cradle for receipt of the transverse end 46 of the shear web 42.

The transverse end 46 of the shear web 42 may be variously received within the channel structure 50. In the embodiment of FIGS. 4 and 5, the transverse end 46 is spaced from the spar cap 32 (which is exposed) and is encased in bond paste 56 such that the bond paste 56 completely fills any spaces within the channel structure 50. In an alternate embodiment, the space between the transverse end 46 and the spar cap 32 may be free of bond material so as to decrease the overall amount and weight of the bond paste.

In the embodiment of FIGS. 6 and 7, the transverse end 46 is also completely encased in bond paste 56 within the closed-ended channel structure 50.

As mentioned, the present invention also encompasses various method embodiments for connecting a shear web 42 between spar caps 32 of upper and lower shell members 20, 22 in a wind turbine blade. The method includes locating a channel structure 50 on each of the spar caps at an attachment location for the shear web, with the channel structures having side walls 52 that flex outwardly relative to longitudinal sides 44 of the shear web. An actuation line 70 is attached between the sides walls 52 of the channel structure 50. Bond paste 56 is deposited into the channel structure 50 between the side walls 52. A transverse end 46 of the shear web 42 is inserted into the channel structure and engages the actuation line 70 such that further movement of the transverse end into the channel structure causes the sides walls to flex inwardly and engage against the longitudinal sides of the shear web, with the bond paste being displaced and distributed between the side walls and longitudinal sides of the shear web.

While the present subject matter has been described in detail with respect to specific exemplary embodiments and methods thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

Actuation lines, such as strings, cables, lines, and the like, are attached to the head and are led out from the shell member beyond the leading or trailing edge.

| Reference Character | Component |
| --- | --- |
| 10 | Wind turbine |
| 12 | Tower |
| 14 | Nacelle |
| 16 | Blades |
| 18 | Rotor hub |
| 20 | Upper shell member |
| 22 | Lower shell member |
| 24 | Leading edge |
| 25 | Internal cavity |
| 26 | Trailing edge |
| 32 | Spar cap |
| 40 | Connection assembly |
| 42 | Shear web |
| 44 | Side |
| 46 | Transverse end |
| 48 | Spring flange member |
| 50 | Channel structure |
| 52 | Side wall |
| 53 | Flexure point |
| 54 | Flared end |
| 56 | Bond paste |
| 58 | Side wall width |
| 60 | Shear web width |
| 62 | Flange member |
| 64 | Attachment leg |
| 66 | Bond face |
| 68 | End wall |
| 70 | Bond length |
| 72 | Actuation line |
| 74 | External fastener |

What is claimed is:

1. A wind turbine blade, comprising:
   an upper shell member having a spar cap configured on an internal face thereof;
   a lower shell member having a spar cap configured on an internal face thereof;
   a shear web extending between said spar caps along a longitudinal length of said blade;
   a connection assembly between transverse ends of said shear web and said spar caps, said connection assembly further comprising:

a channel structure configured on said spar cap, said channel structure comprising side walls that extend from said spar cap at an angle away from longitudinal sides of said shear web, said side walls being flexible so as to move into engagement against said longitudinal sides of said shear web;

a pliant actuation line attached between said side walls of said channel structure;

bond paste disposed within said channel structure; and wherein upon movement of the transverse end of said shear web into said channel structure, said shear web engages said actuation line and pulls said side walls into engagement against said longitudinal sides of said shear web with said bond paste being distributed between said side walls and said longitudinal sides of said shear web.

2. The wind turbine blade of claim 1, wherein said channel structure side walls have a respective base and are spaced apart at said bases, said sides walls flexed outwardly from said respective base for insertion of said shear web into said channel structure.

3. The wind turbine blade of claim 1, wherein at each connection assembly, said channel structure side walls are separate components separately attached to said spar cap.

4. The wind turbine blade of claim 3, wherein said channel structure side walls comprise a respective transversely extending flange member bonded to said spar cap.

5. The wind turbine blade of claim 1, wherein said channel structure comprises an end wall extending between said channel structure side walls, said end wall bonded to said spar cap.

6. The wind turbine blade of claim 1, wherein said transverse end of said shear web is spaced from said spar cap and encased in bond paste within said channel structure.

7. The wind turbine blade of claim 1, wherein each said side wall of said channel structure forms a bond with said longitudinal sides of said shear web having a length that is greater than a width of said transverse end of said shear web.

8. The wind turbine blade of claim 1, wherein said actuation line comprises a string member.

9. The wind turbine blade of claim 8, wherein said string member extends through said channel structure side walls and is attached to an external side of said side walls.

10. A method for connecting a shear web between spar caps of upper and lower shell members in a wind turbine blade, said method comprising:

locating a channel structure on each of the spar caps at an attachment location for the shear web;

the channel structure having sides walls that flex outwardly relative to longitudinal sides of the shear web;

the channel structure having an actuation line attached between the sides walls of the channel structure;

depositing an amount of bond paste into the channel structure between the side walls; and inserting a transverse end of the shear web into the channel structure and engaging the actuation line such that further movement of the transverse end into the channel structure causes the sides walls to flex inwardly and engage against the longitudinal sides of the shear web with the bond paste being displaced and distributed between the side walls and longitudinal sides of the shear web.

11. The method as in claim 10, comprising defining the channel structure by attaching separate spaced-apart members to the spar cap, with the spar cap exposed between the members and the transverse end of the shear web bonded to the spar cap between the members.

12. The method as in claim 10, comprising defining the channel structure by attaching a single integral component to the spar cap, the component having an end wall attached to the spar cap and the transverse end of the shear web is spaced from the end wall and encased in bond paste within the channel structure.

13. The method as in claim 10, comprising providing the actuation line with any combination of length and elasticity so that the transverse end seats completely within the channel structure with the side walls engaged against the longitudinal sides of the shear web.

\* \* \* \* \*